United States Patent [19]
Quadrini

[11] Patent Number: 5,112,326
[45] Date of Patent: May 12, 1992

[54] ADJUSTABLE DIAPER

[76] Inventor: Giuseppe Quadrini, 5270 des Tilleuls, Montreal, Quebec, Canada, H1T 2H6

[21] Appl. No.: 715,385

[22] Filed: Jun. 14, 1991

Related U.S. Application Data

[63] Continuation-in-part of Ser. No. 623,120, Dec. 6, 1990, abandoned.

[51] Int. Cl.5 .................. A61F 13/15; A61F 13/20
[52] U.S. Cl. .................. 604/391; 604/385.1
[58] Field of Search .................. 604/389–391

Primary Examiner—Randall L. Green
Assistant Examiner—R. Clarke
Attorney, Agent, or Firm—Roland L. Morneau

[57] ABSTRACT

An adjustable diaper for babies is provided with a pair of VELCRO tapes on the front flap and a strip of cloth to alternately cover one side of the flap for shielding the babies skin from the VELCRO tape.

7 Claims, 6 Drawing Sheets

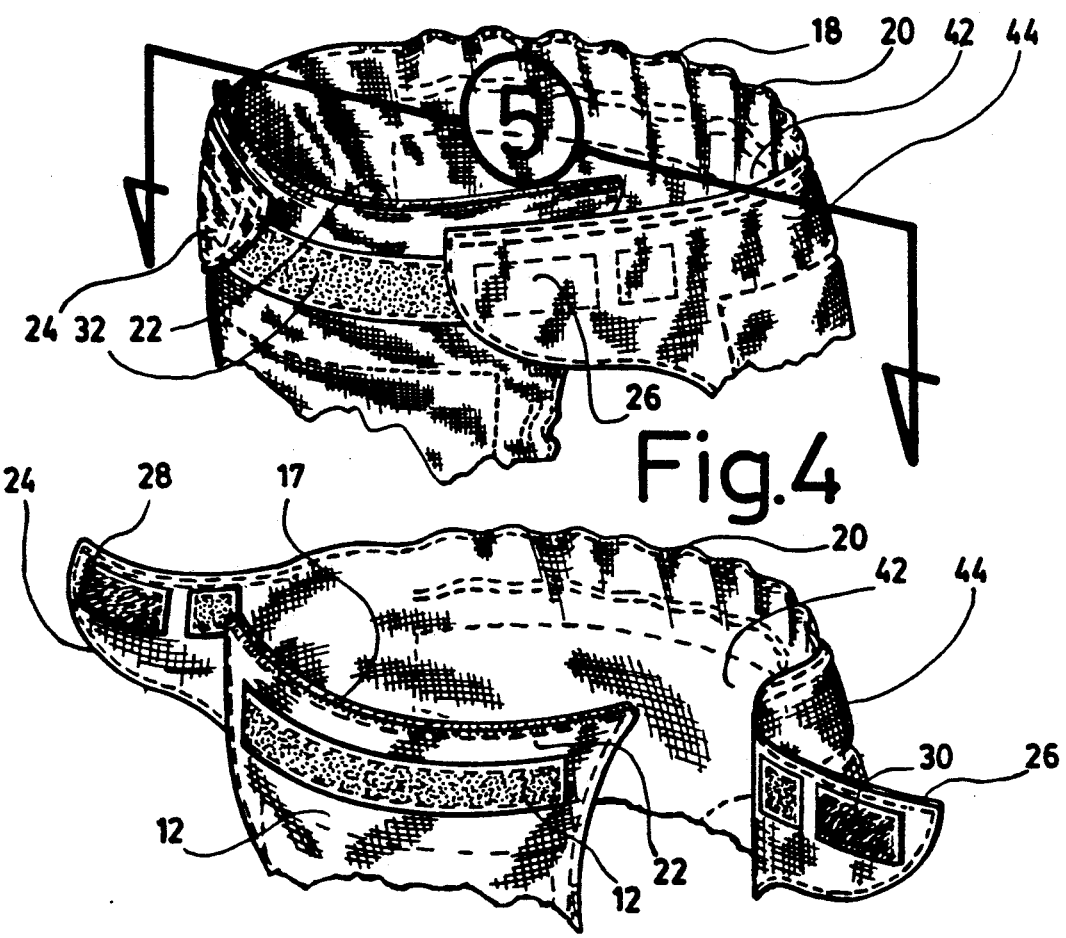
Fig.4
Fig.6
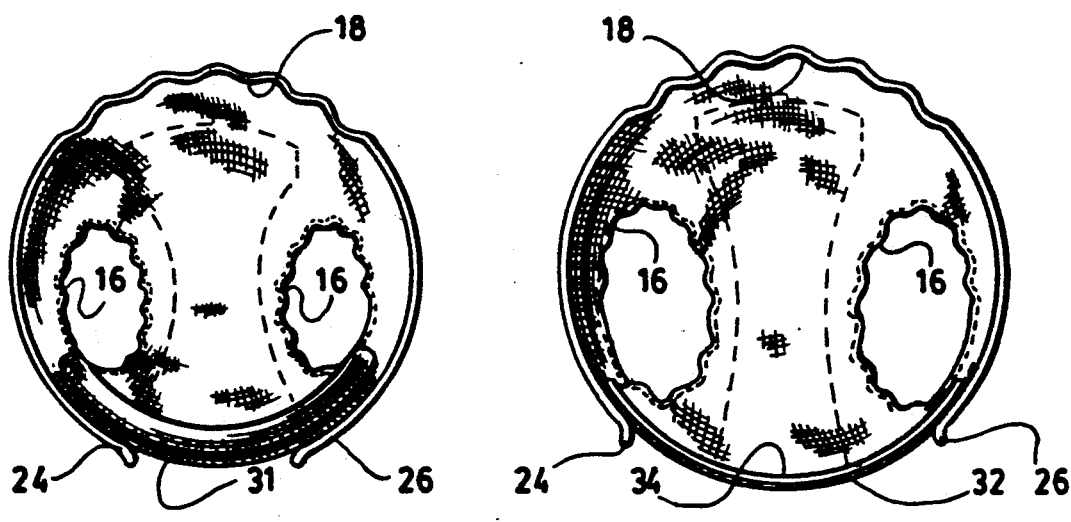
Fig.3
Fig.5

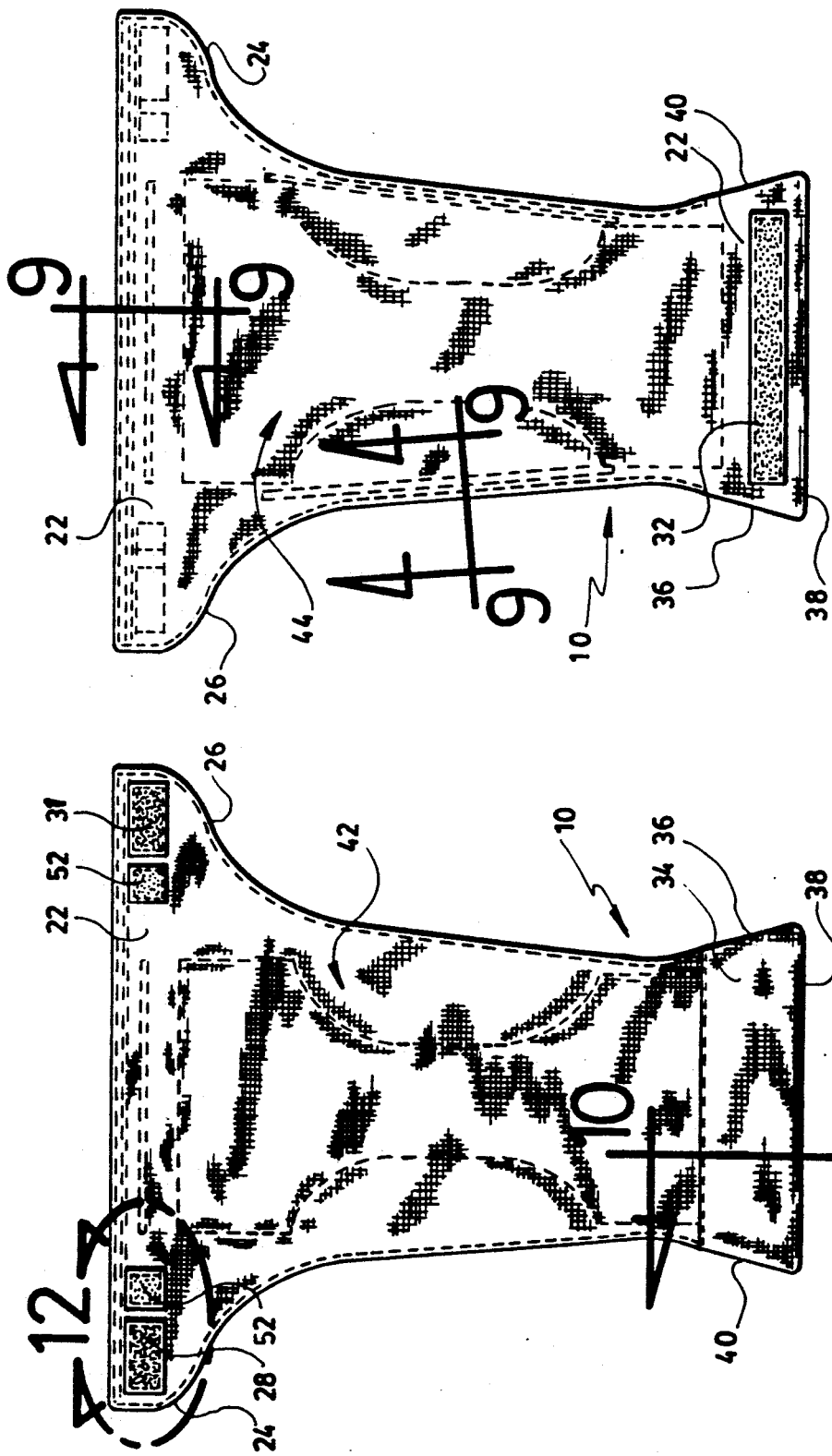

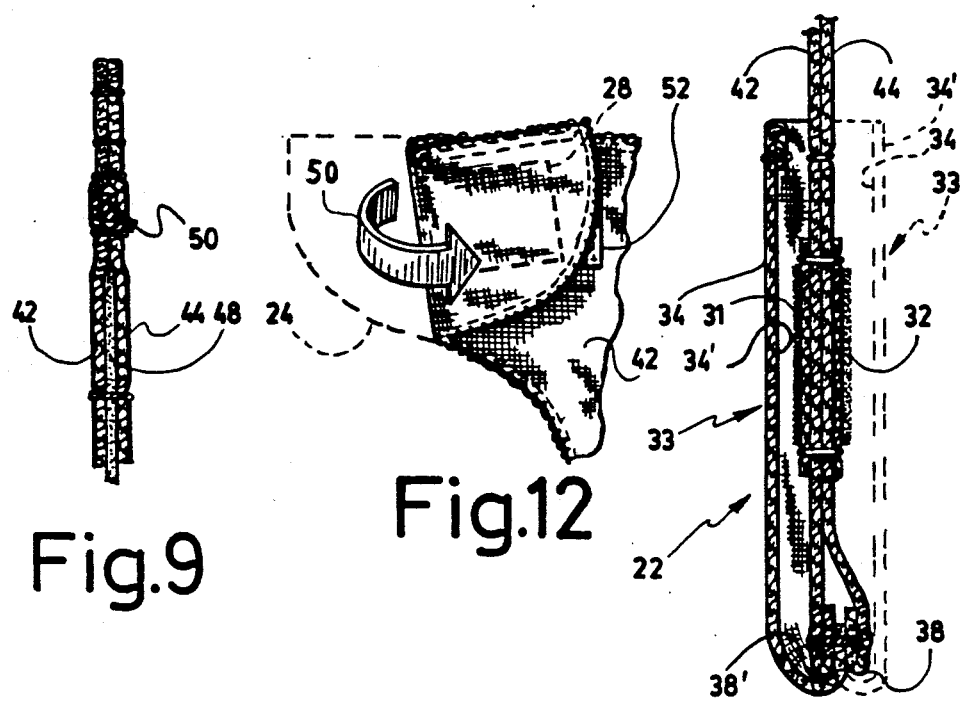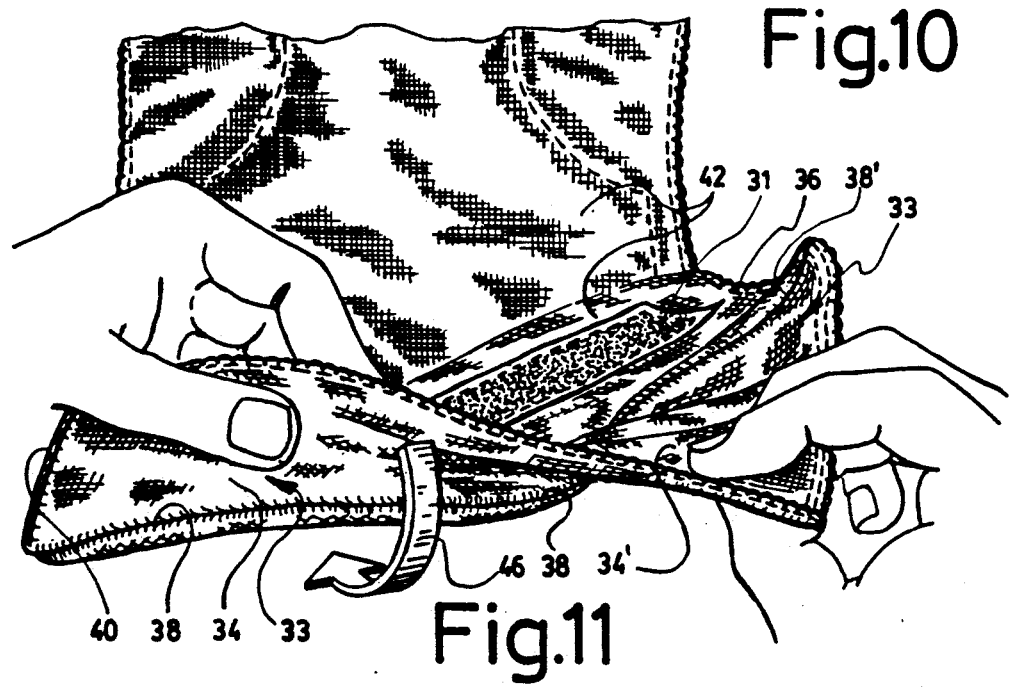

ADJUSTABLE DIAPER

The present application is a continuation-in-part of original application Ser. No. 623,120 filed on Dec. 6, 1990 abandoned.

BACKGROUND OF THE INVENTION

1. Field of the Invention

The invention relates to a diaper attachment system which allows a diaper to be adjustable so that one diaper is applicable to a wide range of body sizes. The diaper is provided with a pair of strips of hook and loop fasteners on the front flap which can be selectively attached to corresponding fasteners on the breech portion of the diaper. A piece of cloth which is attached to the upper edge of the front flap is used to cover one of the fastener strips which is directed inwardly towards the infant's skin.

2. Prior Art

It is common for diapers to be constructed to specific body sizes; in the case of baby diapers, they are constructed to fit specific ranges of body sizes normally based on weight. Diapers of this nature on the part of the manufacture increase the cost of production, inventory and marketing, while for the consumer in the case of baby diapers require that new diapers be purchased as a baby grows and for adult consumers the diapers may be uncomfortable due to their fixed size.

These disadvantages have been overcome by diapers available on the market which can be adjusted to two sizes. Some diapers are provided with a plurality of fasteners which are disposed at various locations on the diapers so that they can fit different body waists.

Some diapers make use of strips of hook and loop fasteners, such as VELCRO, vertically superposed and located on the outer side of the front flap of the diaper. With this arrangement, the upper strip is used for older babies such as between 7 to 15 kilograms while the lower strip can accommodate newborns to 7 kilograms. However, in this latter arrangement, the upper ledge of the front flap remains unsupported. It extends towards the chest of the baby and usually falls forwardly in an unethical fashion. Furthermore, the fastener which has a rough surface is liable to come in contact with the delicate skin of the baby.

SUMMARY OF THE INVENTION

The diaper, according to the present invention, is made of a piece of cloth having a front lap and a breech portion which respectively cover the front and the rear of an infant's bassin. According to a first embodiment, the front and the rear surface of the upper ledge of the front lap is provided with fastening means adapted to hook selectively with corresponding fastening means located on the inner surface of both corners of the upper ledge of the breech portion. According to a second embodiment, the two fastening means are adjacently disposed on the front surface of the front lap, one above the other.

In the first embodiment, the fastening means located on the front lap are alternatively covered by a strip of cloth secured along the upper edge of the front lap. The strip of cloth is intended to cover the fastening means on the rear face when the diaper is fully extended which applies, for example, to a grown up baby. To obtain a smaller size, for example in the case of a newborn infant, the same diaper is used with the strip of cloth flipped forwardly, covering the fastening means located on the front surface of the diaper. The upper ledge of the front lap is folded forwardly so that the fastening means on the rear surface are displayed forwardly and adapted to be hooked by corresponding fastening means on the breech portion. This fold has a twofold advantage: it reduces both the height of the front lap and the girth of the waist.

In the second embodiment, the strip of cloth which is similarly secured along the upper edge of the front lap, can also be flipped, selectively on the front or rear surface of the front lap. However, the strip of cloth is adapted to cover only the upper fastening means when the latter is folded backwardly. In this position, the strip of cloth shields the skin of the infant against the rugosity of the upper fasteners means, and leaves the lower fastening means forwardly exposed.

The fastener means intended for use in this invention make use of a male and a female part such as a snap fastener or a hook and loop such as the fastener known by the trademark VELCRO.

It should be also understood that the fastening means and its corresponding counterpart can be reversibly positioned on the front lap and on the breech portion. Also the fastening means can be located on the back breech and alternatively covered by a strip of cloth secured along the upper edge of the front breech while its corresponding counterpart is positioned on the front lap.

BRIEF DESCRIPTION OF THE DRAWINGS

FIG. 3 is a top view along arrow 3 shown in FIG. 1;

FIG. 4 is a perspective view of the upper part of the diaper of FIG. 1, with the upper ledge extended upwardly for an older infant;

FIG. 5 is a top view along arrows 5 of FIG. 4;

FIG. 6 is a perspective view of the top portion of the diaper shown in FIG. 4 in an incompletely folded position;

FIG. 7 is a view of the front face of the diaper, according to the first embodiment of the present invention, shown in a completely unfolded position;

FIG. 8 is a view of the rear face of the diaper shown in FIG. 7;

FIG. 9 is a cross-sectional view along the two cross-sections 9—9 shown in FIG. 8;

FIG. 10 is a cross-sectional view taken along line 10—10 shown in FIG. 7;

FIG. 11 is a perspective view of the upper part of the front ledge of the diaper of FIG. 1, illustrating a covering strip of cloth in a semi-flipped position;

FIG. 12 is a front view of a wing portion of the upper ledge of the breech portion of the diaper in a folded position;

DETAILED DESCRIPTION OF THE INVENTION

Figure 1:
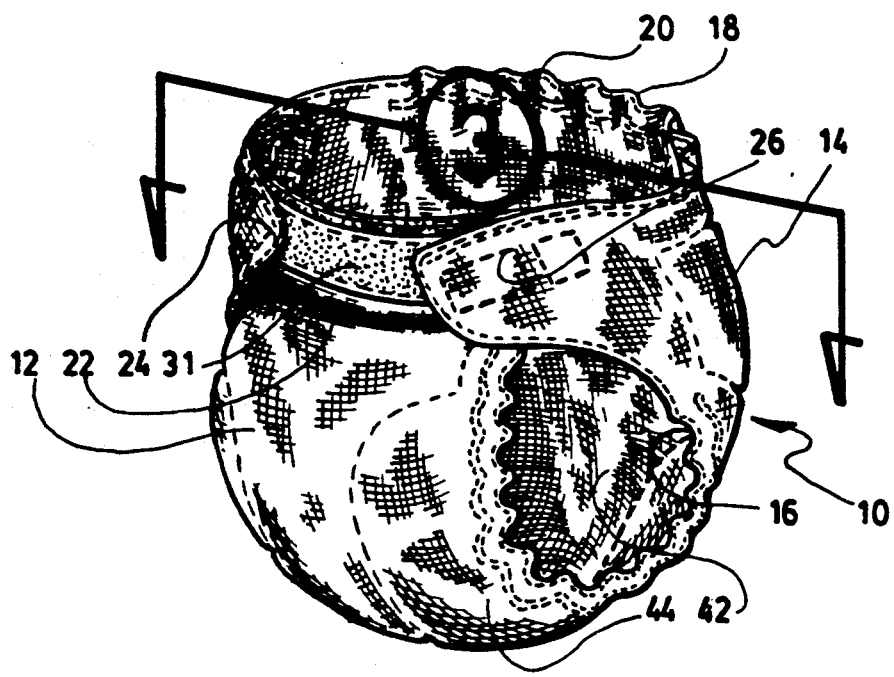
FIG. 1 is a perspective view of a diaper for a newborn baby, according to a first embodiment of the present invention.

FIG. 1 illustrates a diaper 10 having a front lap 12 and a breech portion 14 folded to provide leg openings 16 and a waist opening 18. The waist opening 18 is surrounded at the rear by the upper ledge 20 of the breech portion 14 and by the upper ledge 22 of the lap portion 12. The upper ledge 20 of the breech portion 14 has two laterally extending wing portions 24 and 26 inside of which is mounted a hook and lock fasteners 28 and 30.

Figure 2:
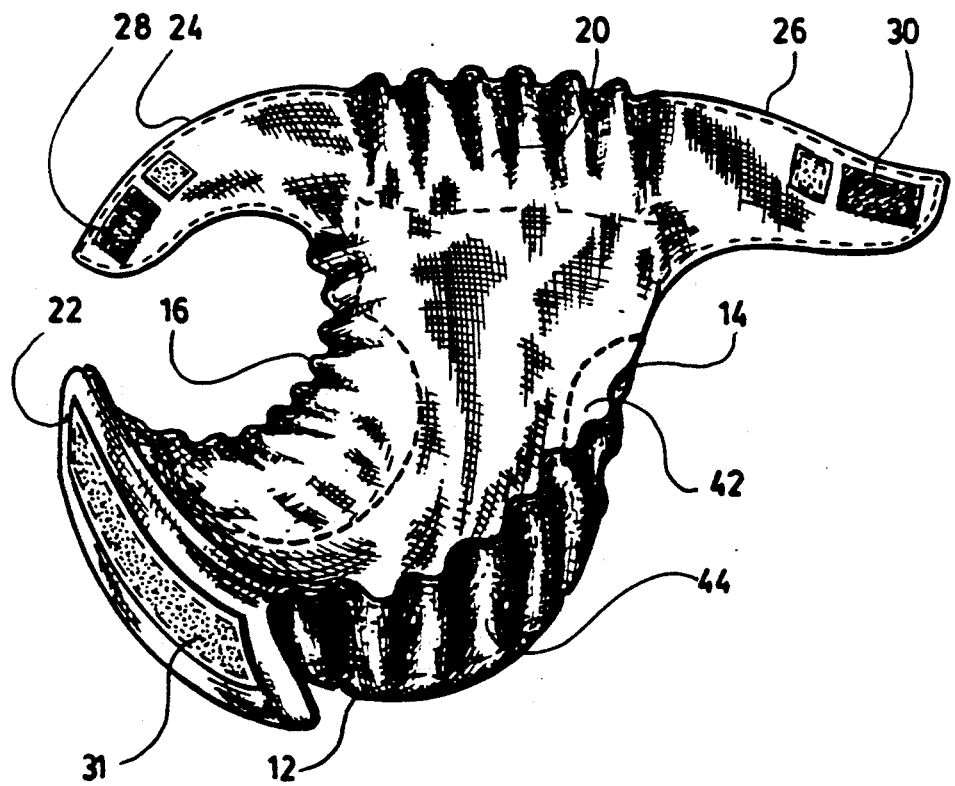
FIG. 2 is a perspective view of the diaper in a semi-unfolded position from the one shown in FIG. 1.

As illustrated in FIG. 2, the upper ledge 22 of the front lap 12 is folded downwardly and is provided on its face projecting outwardly a hook and lock fastener 30.

The hook and lock fastener will be referred to in the remaining part of the description by the expression VELCRO tapes, the word VELCRO being a registered trademark.

The diaper is secured around the waist by contacting the VELCRO patches 28 and 30 over the VELCRO tape 30 according to the size of the thighs and the waist of the baby.

The diaper described in FIGS. 1, 2 and 3, with the upper ledge 22 folded forwardly, is used to obtain a smaller size as in the case of newborn babies because the folding of the upper ledge 20 reduces the size of the openings 16 and 18. To obtain a larger size as in the case where the baby grows older, that is, becomes heavier than about 7 kgs, the folded upper ledge 22 is unfolded as shown in FIGS. 4, 5 and 6. The upper ledge 22 is provided on its front surface with a VELCRO tape 32 which is disposed along the edge 17. The edge 17 is generally rectilinear as well as the VELCRO tapes 30 and 31 and the latter extend adjacent the edge 17. The two VELCRO tapes 30 and 31 are generally oppositely disposed relative to the upper ledge 22. The tapes 30 and 31 are also sufficiently long to meet and be contacted by the patches 28 and 30.

The fact that the front lap 12 has been extended in length by the unfolding of the upper ledge 22, allows the waist 18 to encircle a larger waist and for the openings 16 to encircle larger thighs as clearly obvious by comparing their sizes in FIGS. 3 and 5.

FIG. 7 illustrates the inner face of the diaper 10 while FIG. 8 illustrates the outer face of the same diaper. The fastener tape 32 appears on the outer face in FIG. 8 but the fastener tape 31 is hidden by a strip of cloth 33 as more particularly shown in FIG. 10. The strip of cloth 33 is sewn around the upper ledge 22 of the front lap 12 around the edges 36, 38—38' (FIG. 10) and 40. The purpose of the strip of cloth 33 is to cover alternatively the fastener tapes 31 and 32 as particularly illustrated in FIGS. 10 and 11. The seams around the edges 36, 38—38' and 40 are invisible as illustrated in FIG. 10. The two layers of cloth 42 and 44 are folded inwardly against the lower edge of the strip of cloth 33 to produce the edges 38 and 38 respectively (FIG. 10).

The cross-section shown in FIG. 10 illustrates the diaper 10 made of the two layers of cloth 42 and 44 which are provided with the two fastener tapes 31 and 32 disposed on opposite surfaces of the diaper and facing each other adjacent the edge 38 of the ledge 22 of the front lap. The strip of cloth 33 is sewn along the edge 38 in between the two inner and outer pieces of cloth 42 and 44 and preferably also along the edges 36, 38—38' and 40 of the ledge 22. This strip of cloth 33 is intended to cover the fastener tape 31 while in position shown in FIG. 10, in full line, and to cover the fastener tape 32 when the strip of cloth is shown along the dotted lines. Considering that fasteners such as VELCRO tapes or snaps can irritate the skin of the baby, the strip of cloth 33 will be flipped on the side adapted to shield the fastener normally contacting the skin of the baby. The outside face 34 of the piece of cloth 33 while on the left-hand side of the ledge 22 become inside face while on the right-hand side of the ledge 22 in FIG. 10.

The reverse applies to side 34' while flipped from one side of the ledge 22 to the other side.

For a more complete illustration of the operation of the strip of cloth 33, FIG. 11 shows the manual operation which consists of flipping the strip of cloth 33 in the direction of the arrow 46, the VELCRO tape 31 which was initially covered by the strip of cloth 33 becomes exposed when the latter is flipped in the direction of the arrow 46 to cover the VELCRO tape 32, shown in FIG. 10, but not appearing in FIG. 11.

From the explanation of the structure, the function and the operation of the strip of cloth 33, one may more clearly understand the two alternative shapes and functions of the diaper shown in FIGS. 1–6. When the diaper is used in the embodiment shown in FIGS. 4, 5 and 6, the VELCRO tape 31 which would be normally in contact with the skin of the baby is covered by the strip of cloth 33 as particularly shown in FIG. 5. When the diaper, for example, is used for a newborn baby, the strip of cloth 33 is flipped over the fastener tape 32 and the ledge 22 of the front lap is folded over the front lap itself to expose the VELCRO tape 31 which will be used to close the diaper with the VELCRO patches 28 and 30 to take the shape as shown in FIG. 1.

FIG. 9 provides an example of the construction of the diaper along the edges such as shown by the cross-section lines 9—9 in FIG. 8. The two pieces of cloth 42 and 44 are generally provided with an inner absorbant lining 48. An elastic band 50 is also provided between the two pieces of cloth 42 and 44 to tighten the legs around the openings 16 and the waist opening 18.

FIG. 12 illustrates the wing portion 24 folded over itself so as to hide the VELCRO tape 28 under certain conditions and especially when laundering the diaper 10. Considering that VELCRO tapes are made of hooks and loops, the VELCRO patch 28 which is made of hooks will adhere to the patch 52 made of loops. The wing portion 24 is merely folded along the arrow 54 to eliminate the wear and tear of both patches 28 and 52.

Although the above description has mainly referred to VELCRO-type fasteners, the invention also applies to snap-type fasteners.

The present invention is directed to a diaper having a front lap adapted to be folded to reduce its size. The front lap has two fastenter strips, one of which is selectively adapted to be covered with a strip of cloth to prevent the irritation of the skin of the baby's belly.

A second embodiment making use of two fastener strips and a flippable piece of cloth is illustrated in FIGS. 13-15, 16 and 16a.

In this embodiment, the two strips 60 and 62 are located on the front surface of the front lap 64. The two strips are adjacently disposed one above the other as shown in FIG. 13, the strip 60 extending along the upper ledge 66 of the front lap 64.

Figure 13:
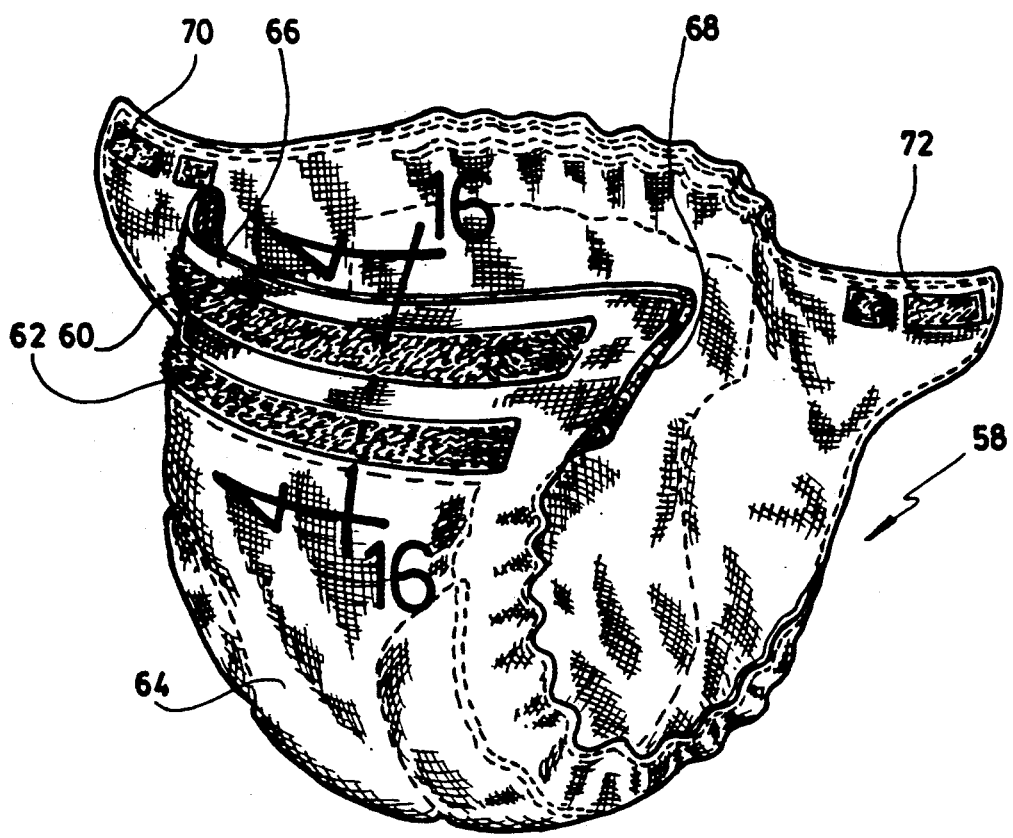
FIG. 13 is a perspective view of a diaper according to a second embodiment.
Figure 14:
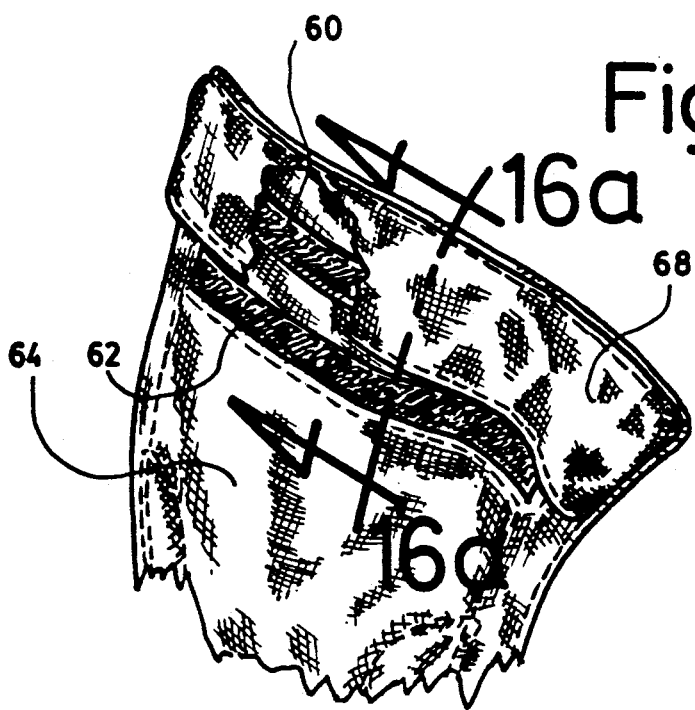
FIG. 14 is a front view of the upper ledge of the front lap with the strip of cloth flipped forwardly.

A strip of cloth 68 is sewn along the upper ledge 66 and is adapted to be flippable from the rear surface as shown in FIG. 13 to the front surface as shown in FIG. 14. The piece of cloth 68 has a minimum width to cover the upper strip 60 and a maximum width so as not to cover the lower strip 62.

Figure 15:
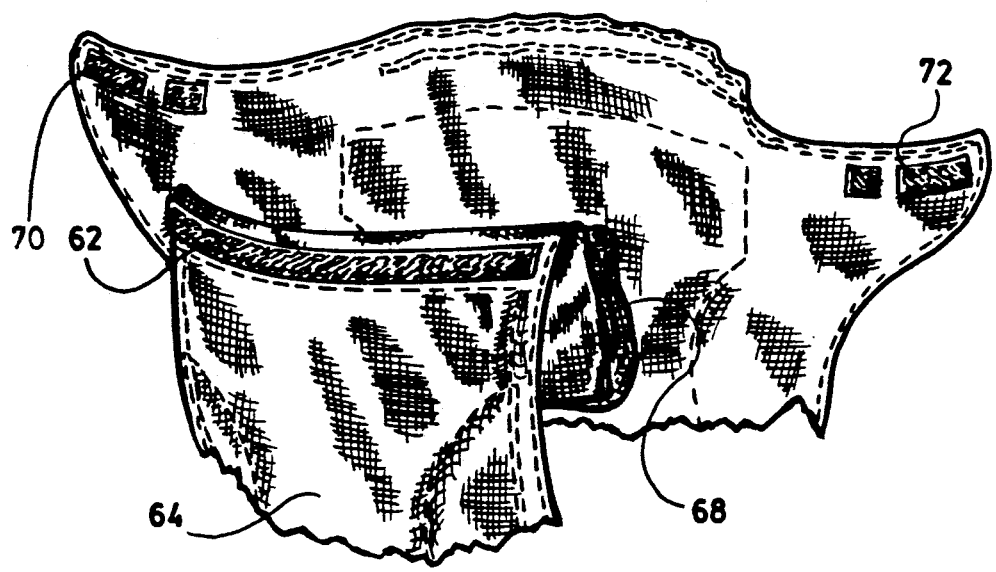
FIG. 15 is a front view of the diaper with the upper fastening means folded backwardly.

When the diaper 58 is intended to be used as a large size diaper, the piece of cloth 68 is flipped backward as in FIG. 13 and the hook and loop fasteners 70 and 72 are folded over the upper strip 60. When the diaper is intended to be used as a small size diaper, the piece of cloth 68 is flipped forwardly to cover the strip 60 as shown in FIG. 14. Subsequently, the upper part of the front lap 64, including the strip 60 and the piece of cloth 68 are folded backwardly as shown in FIG. 15 along a line intermediate between strips 60 and 62. In this latter position, the piece of cloth 68 shields the upper strip 60 and prevents its contact with the infant's belly. Furthermore, the upper part of the front lap 64 being folded inwardly, it reduces the girth of the diaper which is particularly adapted for younger babies. The strip 62 remains forwardly exposed and the patches 70 and 72 can be adheringly folded over the strip 62.

Figure 16:
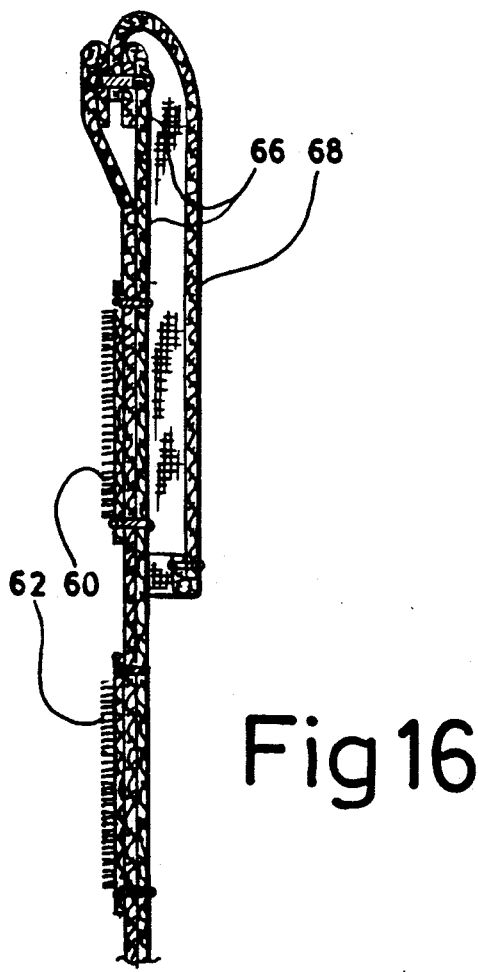
FIGS. 16 and 16a are two cross-sectional views of the front flap with the strip of cloth in the two alternative positions.
Figure 16A:
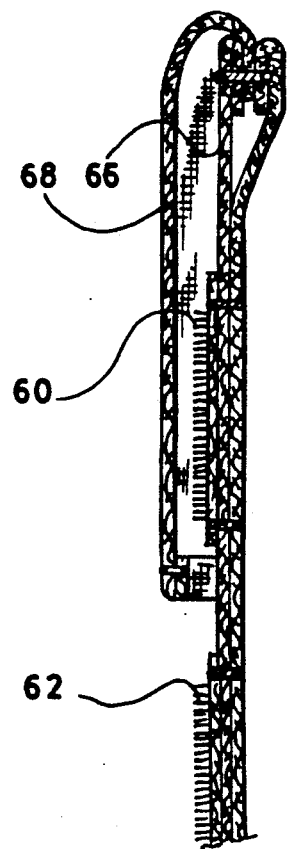

The piece of cloth 68 is sewn to the upper edge of the front lap as shown in FIGS. 16 and 16a and adapted to be reversibly flipped as shown in FIG. 11.

It should also be understood that the tapes 31 and 32 can be either hooks or loops as long as they are adapted to adhere to the patches 28 and 30.

Although the present adjustable diaper has been described for young and older babies, the size can be appropriately made for adults of different sizes.

I claim:

1. An adjustable size diaper made of a piece of cloth having a front lap and a breech portion adapted to cover the front and the rear of an infant's pelvis, said front lap having a substantially rectilinear upper edge, an inner and outer face and a first strip of hook and loop fastener disposed on said outer face below and adjacent said upper edge, said front lap adapted to be folded downwardly along a fold line below and adjacent said first strip for reducing the size of the diaper, a second strip of hook and loop fastener being exposed forwardly on said front lap when the latter is folded along said fold line, a strip of cloth longitudinally fixed to the upper edge of said front lap and adapted to be reversibly folded over the inner and the outer face of said front lap, said strip of cloth having a width sufficient to cover said first strip of hook and loop fastener, whereby said strip of cloth is adapted to cover the one of said strips of hook and loop fastener when facing the infant's pelvis.

2. An adjustable size diaper as recited in claim 1, wherein said second strip of hook and loop fastener is disposed on the outer face of said front lap below and adjacent said first strip of hook and loop fastener, whereby said strip of cloth is adapted to cover said first strip of hook and loop fastener when the flap is folded backwardly along said fold line.

3. An adjustable size diaper as recited in claim 1, wherein said second strip of hook and loop fastener is disposed on the inner face of said front lap opposite said first strip of hook and loop fastener, whereby said strip of cloth is adapted to alternately cover (1) said second strip of hook and loop fastener when the front lap is unfolded and, (2) said first strip when the front flap is folded forwardly.

4. An adjustable size diaper as recited in claim 1, wherein the breech portion has wing portions laterally extending therefrom, a hook and loop fastener patch disposed on each of said wing portions, said wing portions adapted to be folded over one of said strip fasteners exposed forwardly of said diaper.

5. An adjustable size diaper as recited in claim 1, wherein said strip of cloth is laterally fixed to said front flap.

6. An adjustable diaper made of a piece of cloth having a front lap and a breech portion adapted to respectively cover the front and the rear of an infant's pelvis, said front lap having a substantially rectilinear upper edge, a strip of a hook and loop fastener disposed below and adjacent said upper edge of said front lap on opposite faces of said front lap, a strip of cloth longitudinally fixed to said upper edge and adapted to reversibly lie over one of said fasteners and to longitudinally cover one of said fasteners, the upper edge of said breech portion having wing portions laterally extending therefrom, a hook and loop fastener patch disposed on said wing portions on one face thereof, said wing portions adapted to be folded over said upper edge of said front lap to releasably adhere to one of said fastener strips disposed on said front lap.

7. An adjustable diaper made of a piece of cloth having a front lap and a breech portion adapted to respectively cover the front and the rear of an infant's pelvis, said front lap having an inner and outer face, and a substantially rectilinear upper edge, a pair of strips of a hook and loop fastener disposed below said upper edge on said outer face, said strips of fasteners being parallel and spaced from each other, a strip of cloth longitudinally fixed to said upper edge and adapted to reversibly lie on the inner and outer face of said front lap, whereby said strip of cloth is adapted to longitudinally cover the strip of fastener adjacent said edge, when the front lap is folded backwardly along a fold line parallel to and between both strips of fasteners.

* * * * *